(12) United States Patent
Masson et al.

(10) Patent No.: US 10,012,570 B2
(45) Date of Patent: Jul. 3, 2018

(54) MODULE FOR CAPTURING A GAS DISSOLVED IN A LIQUID AND MEASURING DEVICE

(71) Applicant: FRANATECH AS, Oslo (NO)

(72) Inventors: Michel Masson, Vögelsen (DE); Bernward Starke, Adendorf (DE); Jens Gronemann, Lübeck (DE); Thomas Kainz, Lüneburg (DE); Thorsten Jokubeit, Kirchgellersen (DE)

(73) Assignee: FRANATECH AS, Oslo (NO)

( * ) Notice: Subject to any disclaimer, the term of this patent is extended or adjusted under 35 U.S.C. 154(b) by 0 days.

(21) Appl. No.: 15/113,727

(22) PCT Filed: Jan. 22, 2015

(86) PCT No.: PCT/EP2015/051209
§ 371 (c)(1),
(2) Date: Jul. 22, 2016

(87) PCT Pub. No.: WO2015/110507
PCT Pub. Date: Jul. 30, 2015

(65) Prior Publication Data
US 2017/0010189 A1    Jan. 12, 2017

(30) Foreign Application Priority Data
Jan. 24, 2014    (FR) ...................................... 14 50601

(51) Int. Cl.
*B01D 19/00*    (2006.01)
*G01N 1/22*    (2006.01)
*G01N 1/40*    (2006.01)

(52) U.S. Cl.
CPC ........... *G01N 1/22* (2013.01); *B01D 19/0031* (2013.01); *G01N 1/4005* (2013.01)

(58) Field of Classification Search
CPC .. B01D 19/0031; B01D 61/36; B01D 61/362; G01N 1/22; G01N 1/4005; H01J 49/0427; H01J 49/0436
See application file for complete search history.

(56) References Cited

U.S. PATENT DOCUMENTS 3,830,106 A * 8/1974 Gardiner ................ B01D 61/28
                                                                210/321.6
4,293,399 A * 10/1981 Belanger ............ G01N 27/4045
                                                                204/415

(Continued)

OTHER PUBLICATIONS

Search Report from FR Intellectual Property Office (INPI) on related FR application (FR1450601) dated Oct. 8, 2014.

(Continued)

*Primary Examiner* — Jason M Greene
(74) *Attorney, Agent, or Firm* — Klein, O'Neill & Singh, LLP

(57) ABSTRACT

The invention relates to a module for capturing at least one gas dissolved in a liquid (L), arranged so as to be mounted on a body (12) of a device (10) for measuring the value of at least one parameter of said gas, said capturing module (20) comprising a gas circulation base arranged so as to be mounted on said body (12), the capturing module (20) being characterized in that it comprises a housing for receiving at least one membrane, defining an opening and projecting from said base, and at least one membrane mounted in said housing so as to extend inside said opening in order to capture the gas dissolved in the liquid (L).

20 Claims, 3 Drawing Sheets

(56) References Cited

U.S. PATENT DOCUMENTS

| | | | | |
|---|---|---|---|---|
| 4,537,740 | A | * | 8/1985 | Colburn ............. B01D 19/0031 376/253 |
| 4,821,585 | A | * | 4/1989 | Kempe ................ G01N 1/2247 210/321.87 |
| 5,104,810 | A | * | 4/1992 | Birbara ............. B01D 19/0031 422/89 |
| 5,324,938 | A | | 6/1994 | Hambitzer et al. |
| 5,703,359 | A | * | 12/1997 | Wampler, III ...... H01J 49/0427 250/288 |
| 6,360,588 | B1 | * | 3/2002 | Ross ................... H01J 49/0436 73/38 |
| 6,666,099 | B2 | * | 12/2003 | Taylor ................ G01N 33/2823 73/863.12 |
| 2005/0005674 | A1 | * | 1/2005 | Gilbert .................... G01N 1/22 73/19.12 |
| 2007/0266800 | A1 | * | 11/2007 | Risk ........................ G01N 1/22 73/863.23 |
| 2017/0165592 | A1 | * | 6/2017 | Hunter ............... B01D 19/0031 |

OTHER PUBLICATIONS

Bauer, Scott, "Membrane introduction mass spectrometry; an old method that is gaining new interest through recent technological advances", TRAC, Trends in Analytical Chemistry, May 1, 1995, pp. 202-213, vol. 14, No. 5, Elsevier, Amsterdam, NL.

Hoch, George et al., "A Mass Spectrometer Inlet System for Sampling Gases Dissolved in Liquid Phases", Archives of Biochemistry and Biophysics, Apr. 1, 1963, pp. 160-170, vol. 101, No. 1, Academic Press, US.

Lapack, Mark A. et al., "Valved Sampling Cell for Membrane Introduction Mass Spectrometry", Analytical Chemistry, Sep. 1, 1996, pp. 3072-3075, vol. 68, No. 17, American Chemical Society, US.

Tortell, Philippe D., "Dissolved gas measurements in oceanic waters made by membrane inlet mass spectrometry", Limnology and Oceanography: Methods, Jan. 1, 2005, pp. 24-37, vol. 3, American Society of Limnology and Oceanography, Inc., US.

* cited by examiner

MODULE FOR CAPTURING A GAS DISSOLVED IN A LIQUID AND MEASURING DEVICE

FIELD OF ART

The invention relates to the field of measuring the value of a parameter of a gas dissolved in a liquid, and more particularly relates to a module for capturing at least one gas dissolved in a liquid, as well as a device for measuring the value of at least one parameter of said gas comprising such a capturing module.

BACKGROUND

It is known to measure the value of one or more parameters of a gas dissolved in a liquid, for example its concentration or its pressure. As an example, it is known to measure the concentration of methane or carbon dioxide in oceans or lakes, for example to determine the influence of pollution on those environments, or to determine the pressure of a gas near a pipeline in order to detect any leaks.

In order to perform such measurements, a measuring device comprises, in a known manner and as illustrated in FIG. 1, a cylindrical body 2 inside which a measuring sensor (not shown) is mounted for measuring the value of the parameter(s) to be measured.

The cylindrical body 2 comprises, at one of its ends 2a, a membrane 3 for capturing gases dissolved in a liquid L in which the device 1 is submerged, maintained on the body 2 by a maintaining element 4. Such a membrane 3 allows the gases dissolved in the liquid L to penetrate the inside of the body 2 of the device 1.

In order for the membrane 3 to be able to withstand the pressure of the liquid L and not tear, it is known to add, between the membrane 3 and the cylindrical body 2, a support element 5 for the membrane 3 assuming the form of a porous metal disc.

The maintaining element 4 is mounted bearing on a transverse inner wall 2b of the end 2a of the body 2, for example by screwing or using a plurality of screws (not shown) in order to maintain the membrane 3 and the support element 5 on the body 2. Such a maintaining element 4 ordinarily assumes the form of a ring defining a cylindrical central opening 4a, the dual function of which is to maintain the membrane 3 and the support element 5 on the end 2a of the body 2 while allowing the liquid L to come into contact with the membrane 3 via the central opening 4a.

In order to make the device 1 tight with respect to the liquid L and thereby prevent the liquid L from penetrating the inside of the cylindrical body 2, the device 1 comprises, still in reference to FIG. 1, a first O-ring 7 arranged between the end 2a of the body 2 and the maintaining element 4 and a second O-ring 8 arranged between the membrane 3 and the maintaining element 4.

The body 2 of the device lastly comprises an inlet conduit 9a making it possible to convey the gas coming from the liquid L from the porous support element 5 to the measuring sensor and an outlet conduit 9b making it possible to convey the gas from the measuring sensor to the porous support element 5 so that it returns into the liquid L.

During the mounting of the device 1, the support element 5 is first arranged on the end 2a of the body 2, then the membrane 3 is placed on the support element 5, and lastly the maintaining element 4 is mounted on the body 2 in order to make the device 1 impermeable to the liquid L while allowing the gas dissolved in the liquid to penetrate inside the body 2.

During the operation of the device 1, the gas dissolved in the liquid L traverses the membrane 3 of the liquid L, then the porous support element 5, and is next conveyed to the measuring sensor by the inlet conduit 9a so that the sensor can determine the value of the parameter(s) of the gas to be measured. Once the measurement is done by the sensor, the gas is conveyed by the outlet conduit 9b from the sensor to the porous support element 5 and the membrane 3, which it traverses up to the liquid L.

However, in such a device, the gas exchange at the membrane 3 between the liquid L and the inlet conduit 9a is not very effective, since the exchange surface between the inlet conduit 9a and the porous support element 5 is relatively small, the surface of the opening of the inlet conduit being much smaller than the surface of the porous support element 5, which does not allow a satisfactory circulation of the gas in the device 1 and is therefore a drawback.

One obvious solution would be to increase the exchange surface, in particular by increasing the dimensions of the inlet conduit. Such an increase is not, however, satisfactory, since it increases the response time of the device, i.e., the time necessary for the sensor to measure the value of the parameter(s) of the studied gas, which is a significant drawback.

SUMMARY

The present invention aims to resolve at least some of these drawbacks by proposing a module for capturing a gas dissolved in a liquid that is both effective and reliable while allowing a low response time of the device.

To that end, the invention first relates to a module for capturing at least one gas dissolved in a liquid arranged to be mounted on a body of a device for measuring the value of at least one parameter of said gas, said capturing module comprising a gas circulation base arranged to be mounted on said body, the capturing module being remarkable in that it comprises a housing for receiving at least one membrane, defining an opening and projecting from said base, and at least one membrane, preferably circular, mounted in said housing so as to extend in said opening in order to capture the gas dissolved in the liquid.

The projection of the housing advantageously allows the membrane to extend in the liquid such that the gas or gases traversing the membrane are no longer necessarily guided perpendicular thereto and can consequently be guided toward an inlet conduit having a larger exchange surface, not necessarily situated below the membrane, perpendicular thereto.

The housing advantageously extends obliquely from the base, preferably perpendicular to said base in order to make it easy to capture and convey the gas.

Advantageously, the capturing module comprises a porous membrane support element arranged in the opening of the housing and through which the gas can circulate. Such a support element makes it possible to prevent the membrane from tearing when it is subject to the movements of the liquid in which the capturing module is submerged.

The housing and the base are advantageously configured to allow the fluid communication in gaseous phase between the support element of the membrane and a body of a measuring device. To that end, the capturing module advantageously comprises a gas injection conduit, connecting the support element of the membrane and the base, and which is configured to be in fluid communication with a gas inlet conduit of a body of a measuring device, and a gas discharge conduit, connecting the base to the support element of the membrane and which is configured to be in fluid communication with a gas outlet conduit of a body of a measuring device.

Also advantageously, the support element assumes the form of a planar plate extending in a parallel plane containing the longitudinal axis of the gas injection conduit and the longitudinal axis of the gas discharge conduit. The gas can then circulate both parallel and perpendicular to the plane of the support element, which makes it possible to drastically improve the circulation of the gas and therefore the efficiency of the capturing module and the device on which said capturing module is mounted.

Advantageously, the support element comprises, on its periphery, a machined gas outlet wall emerging on the gas injection conduit and a machined gas inlet wall emerging on the gas discharge conduit.

According to one aspect of the invention, the inlet wall and the outlet wall are diametrically opposite so as to improve the circulation of the gas through the support element of the membrane.

Preferably, the opening of the housing is a through opening and the capturing module comprises two membranes arranged on either side of the support element, which makes it possible to double the gas exchange surface between the liquid and the inside of the capturing module.

According to one feature of the invention, the opening of the housing is circular and the support element assumes the form of a disc, preferably made from metal. Such an arrangement is easy to manufacture and use in order to capture a gas dissolved in a liquid.

Also preferably, the body of the device comprising at least one end, the capturing module is arranged to be mounted on said end.

According to one feature of the invention, the body of the device being cylindrical with a circular section, the base assumes the form of a circular element arranged to be mounted on one of the ends of the body.

According to another feature of the invention, the capturing module comprises at least one O-ring, preferably a plurality of O-rings for example arranged on either side of the membrane(s) so that only one gas can traverse the membrane(s) when the capturing module is mounted on a body of a device.

Preferably, the capturing module assumes the form of a stopper for a body of a measuring device, preferably at one of its ends, in order to make the device on which the capturing module is mounted impermeable to a liquid in which the device is submerged.

The invention also relates to a device for measuring the value of at least one parameter of at least one gas dissolved in a liquid, said device comprising a hollow body, preferably cylindrical, in which a measuring sensor is mounted, and a capturing module, as previously described, mounted on said body by its base.

The housing of the capturing module advantageously projects from the body of the device so as to effectively capture the dissolved gas.

According to one feature of the invention, the body of the device comprises a gas inlet conduit connecting the gas injection conduit of the capturing module to the measuring sensor and a gas outlet conduit connecting the measuring sensor to the gas discharge conduit of the capturing module.

Preferably, the body of the device being cylindrical, the membrane extends in a plane parallel to the longitudinal axis of said cylindrical body such that the gas is captured perpendicular to the circulation direction of the gas in the device, which improves the efficiency of the device.

The capturing module can be mounted on any part of the body of the measuring device, such as an end or a wall.

In one preferred embodiment of the device according to the invention, the capturing module assumes the form of a stopper mounted on one end of the body of the measuring device. The assembly and locking of a measuring device with such a stopper is quick and easy because it is no longer necessary to mount the membrane and the support element, or even the O-rings, separately from the stopper.

Other features and advantages of the invention appear in the following description, done in light of the appended figures provided as non-limiting examples and in which identical references are given to similar objects.

DESCRIPTION OF ONE PREFERRED EMBODIMENT OF THE SYSTEM ACCORDING TO THE INVENTION

I. Measuring Device 10

The device according to the invention is designed and arranged to be submerged in a liquid in order to measure the value of at least one parameter of at least one gas dissolved in said liquid, such as measuring a concentration or pressure value of said gas. Such a gas may for example be methane or carbon dioxide, dissolved in seawater or freshwater.

In the preferred embodiment of the device according to the invention illustrated in FIGS. 2 to 6, the measuring device 10, submerged in this example in a liquid L, comprises a body 12 and a gas capturing module 20.

a) Body 12

Figure 1:
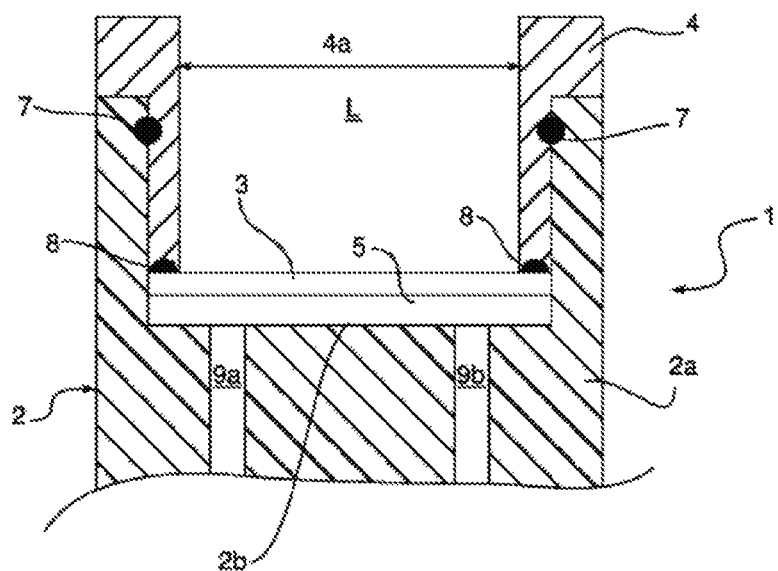
FIG. 1 (already discussed) is a diagrammatic longitudinal sectional view of a device for measuring the pressure of a gas dissolved in a liquid of the prior art.
Figure 2:
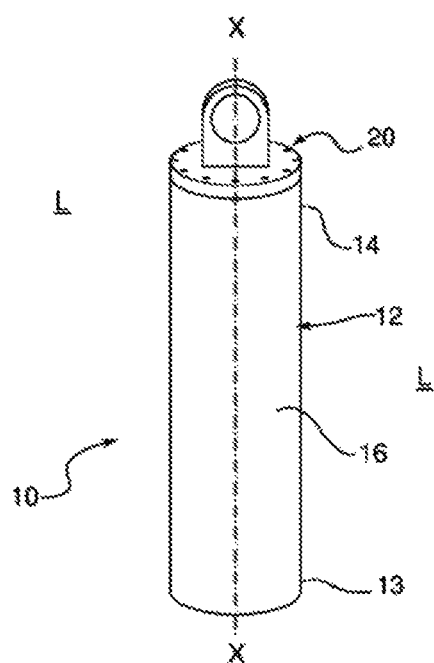
FIG. 2 is a partial diagrammatic perspective view of one embodiment of the device according to the invention.

In reference to FIG. 2, the body 12 assumes the form of a hollow cylinder extending along a longitudinal axis X and including two ends 13, 14. The gas capturing module 20 is mounted on said body 12 at one 14 of its ends, while the other end 13 is closed off.

A sensor (not shown) for measuring the value of at least one parameter of at least one gas dissolved in the liquid L is mounted inside the hollow body 12.

Figure 4:
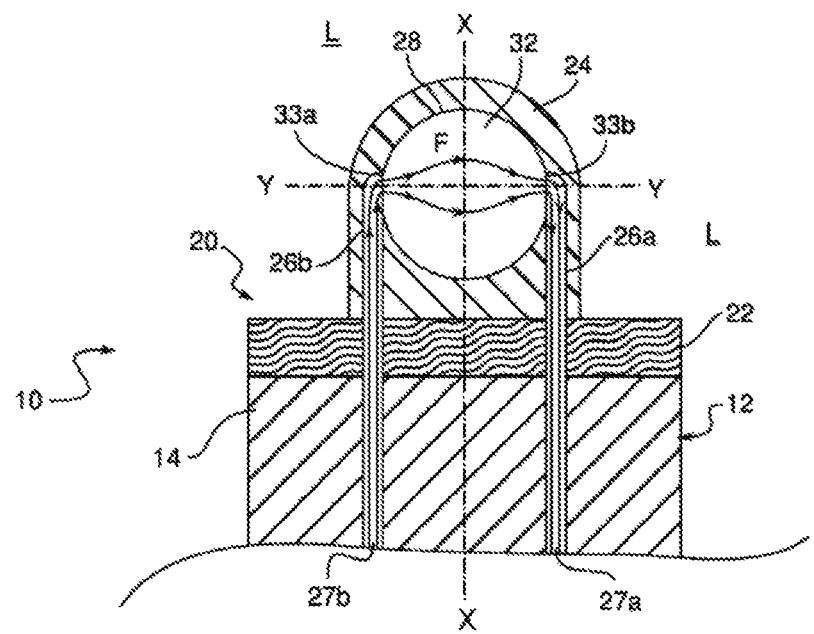
FIG. 4 is a partial diagrammatic longitudinal sectional view of the device of FIG. 2.

In reference to FIG. 4, the hollow body 12 further comprises a gas inlet conduit 27a making it possible to convey gas to the measuring sensor so that the latter measures at least one of the parameters of that gas, and a gas outlet conduit 27b making it possible to discharge the gas from the measuring sensor once the parameter measurement(s) are done.

b) Capturing Module 20

The capturing module 20 can be mounted on any part of the body 12 of the measuring device 10, such as an end 14 or a wall 16 (in reference to FIG. 2) and using any appropriate fastening method, for example by welding, by screwing, or using a set of screws. Alternatively, the capturing module 20 can be at least partially integral with the body 12.

The capturing module 20 makes it possible to capture one or several gases dissolved in the liquid L whereof a parameter value must be measured by the measuring sensor. The capturing module 20 therefore allows said gas or gases to circulate from the liquid L toward the inside of the body 12 and from the inside of the body 12 toward the liquid L, the device 10 being impermeable to the liquid L. To that end, the capturing module 20 is configured to allow the fluid communication in gaseous phase with the gas inlet conduit 27a of the body 12 on the one hand, and with the gas outlet conduit 27b on the other hand.

In this example, the capturing module 20 assumes the form of a stopper mounted on one end 14 of the body 12. This is of course not limiting with respect to the scope of the present invention, and it will be noted that the capturing module 20 according to the invention is not necessarily a stopper.

Figure 3:
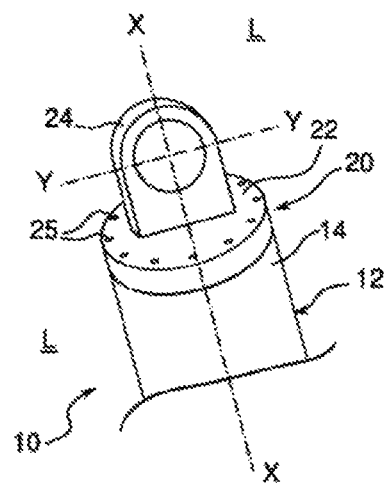
FIG. 3 is a close-up view of the end of the device of FIG. 2.

As illustrated in FIG. 3, the capturing module 20 comprises a base 22 and a housing 24.

i) Base 22

The base 22 makes it possible to mount the capturing module 20 on the body 12 of the device 12. In this example, the base 22 assumes the form of a metallic circular element whereof the outer diameter is substantially the same as that of the cylindrical body 12 and that is fastened on the end 14 thereof using a plurality of screws 25.

The base 22 allows the circulation of a gas from the housing 24 toward the inside of the body 12 and from the inside of the body 12 toward the housing 24.

To that end, as illustrated in FIG. 4, the base 22 and the housing 24 are fluidly connected, on the one hand to the gas inlet conduit 27a by a gas injection conduit 26a, and on the other hand to a gas outlet conduit 27b by a gas discharge conduit 26b, in the longitudinal axes are parallel to one another. The gas injection conduit 26a and the gas inlet conduit 27a are coaxial, as are the gas discharge conduit 26b and the gas outlet conduit 27b.

ii) Housing 24

The housing 24 makes it possible to capture a gas dissolved in a liquid L.

As illustrated in FIG. 3, the housing 24 assumes the form of a metal lug secured to the base 22 and extending protruding from the base 22 along the axis X, perpendicular thereto, and extending widthwise along an axis Y over a distance smaller than the outer diameter of the circular base 22.

Preferably, the housing 24 is integral with the base 22 so as to form a single piece. Alternatively, the housing 24 can be attached on the base 22.

Figure 5:
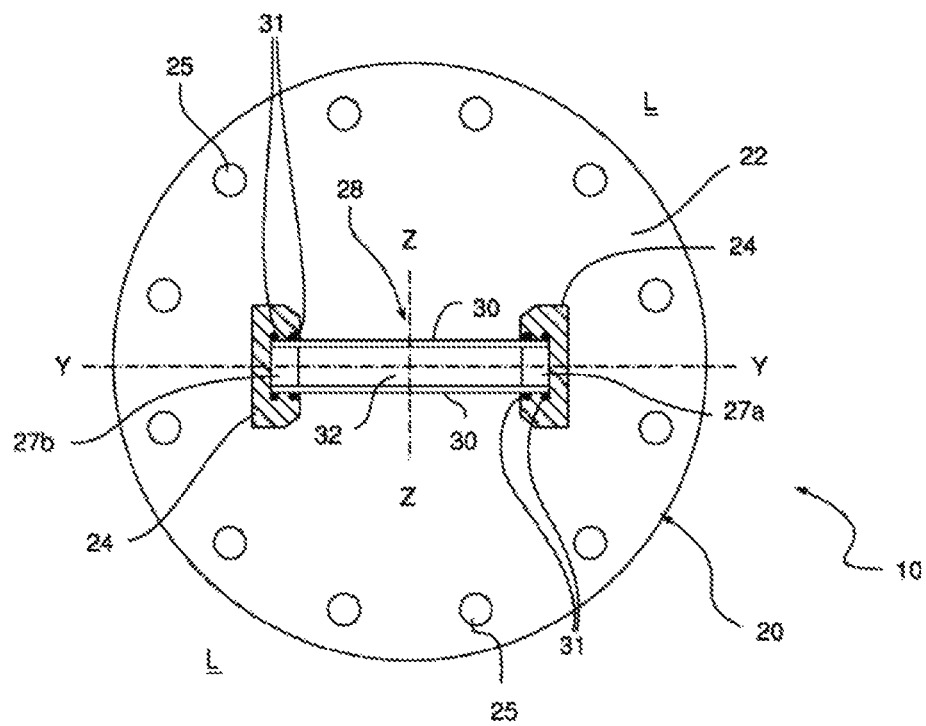
FIG. 5 is a partial diagrammatic transparent top view of the device of FIG. 2.
Figure 6:
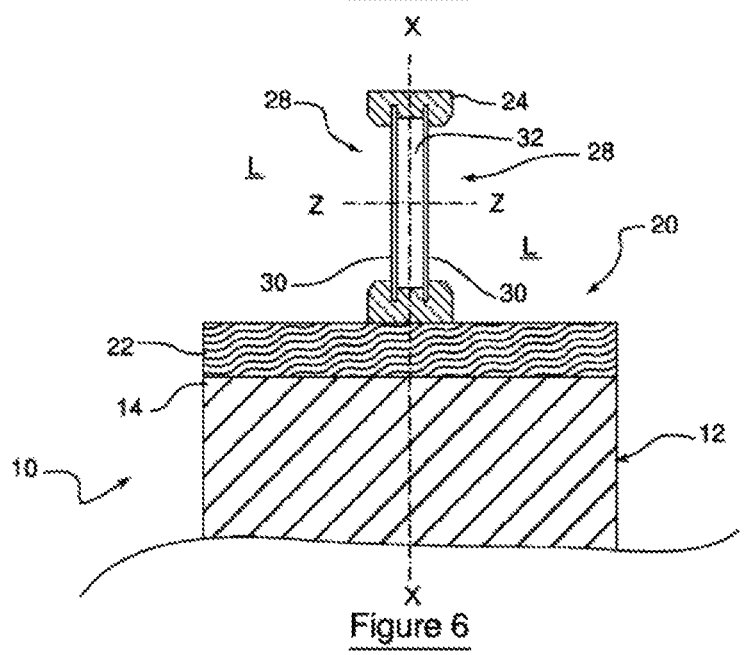
FIG. 6 is a partial diagrammatic transparent profile view of the device of FIG. 2.

As illustrated in FIGS. 4 to 6, the housing 24 defines a through cylindrical opening 28 with longitudinal axis Z. "Through" means that a gas can cross all the way through the opening 28.

As illustrated in FIGS. 5 and 6, two circular membranes 30 each extend entirely in the opening 28 of the housing 24 parallel to the axes X and Y and perpendicular to the axis Z. In other words, the membranes 30 extend in a plane perpendicular to the base 22.

The membranes 30 are in contact with the liquid L in order to capture at least one gas dissolved in the L by the side faces of the housing 24, which offers a large exchange surface to capture the gas or gases dissolved in the liquid L and therefore one wishes to measure at least one of the parameters.

It will be noted, even if it goes without saying, that the junction between the membranes 30 and the lug 24 is impermeable to the liquid L.

In this example, as illustrated in FIG. 5, the capturing module comprises four pairs of sealing gaskets 31 arranged between the housing 24 and the membranes 30. Of course, the number of gaskets may differ in another embodiment of the device according to the invention. Such gaskets may for example be O-rings and made from nitrile rubber (for example, from Perbunan®).

A support element 32, for example in the form of a planar plate, is arranged between the two membranes 30, which are thus pressed on said support element 32 so that they do not tear under the effect of the pressure when the device 10 is submerged in the liquid L.

The support element 32 assumes the form of a porous metal disc, for example made by sintering, allowing the circulation of the gas through the disc both in its thickness along the axis Z (in reference to FIGS. 5 and 6) and transversely along its axis Y in reference to FIGS. 3 and 4.

In reference to FIG. 4, the gas injection conduit 26a and the gas discharge conduit 26b both emerge on the edge of the support element 32 on which the two membranes 30 rest so as to create a gas circulation circuit or flow F, preferably continuous, through the support element 32, the gas injection conduit 26a, the gas discharge conduit 26b, the inlet conduit 27a and the measuring sensor and the gas outlet conduit 27b, such a flow F advantageously being perpendicular to the longitudinal axis of the membranes 30, which improves the injection of the gas captured by the membranes 30 in the flow F.

In order to improve the quality of the circulation of the gas, as illustrated in FIG. 4, two diametrically opposite edges 33a and 33b of the support element 32 have been machined on the periphery of the support element 32 so as to respectively make up an inlet wall 33a in the support element 32, for the gas coming from the gas outlet conduit 27b via the gas discharge duct 26b, and an outlet wall 33b of the support element 32, for the gas to be conveyed to the gas inlet conduit 27a via the gas injection conduit 26a.

Driving means (not shown) for driving the gas flow F can be provided in order to drive the gas in a circulation direction along the circuit.

II. Implementation

A gas dissolved in the liquid L first crosses through one and/or the other of the membranes 30 and penetrates the support element 32, at which it travels to the outlet wall 33b of the support element 32.

The gas is next conveyed from the outlet wall 33b to the measuring sensor via the injection conduit 26a and the inlet conduit 27a.

The sensor then measures at least one value of at least one parameter of said gas.

Once the measurement has been done, the gas is discharged by the measuring sensor to the outlet conduit 27b then, via the discharge conduit 26b, to the inlet wall 33a in the support element 32.

The gas then penetrates inside the support element 32, from which it can traverse one or the other of the membranes 30 toward the liquid L or circulate again toward the measuring sensor while traversing the support element 32 transversely, along its axis Y, up to the outlet wall 33b.

Of course, the measuring device 10 can also operate, mutatis mutandis, in the direction opposite the gas circulation direction illustrated in FIG. 4.

The circulation of the gas flow through the measuring device 10 therefore advantageously constitutes an effective circulation circuit for the gas inasmuch as the capturing of the gas by the membranes 30 is done on a large exchange surface and perpendicular to said flow F.

The present invention therefore makes it possible to increase the gas exchange surface with the liquid L while offering an effective circulation of the gas captured by the membranes to the measuring sensor, making the measuring device reliable, quick, and effective.

It should further be noted that the present invention is not limited to the examples described above and is open to many alternatives accessible to one skilled in the art.

In particular, the shapes, dimensions, natures and characteristics in terms of material of the body 12, the base 22, the housing 24, the membranes 30, the support element 32, the inlet 27a, and outlet 27b conduit(s), as illustrated in FIGS. 2 to 6 so as to illustrate one example embodiment of the invention, cannot be interpreted as being limiting.

The invention claimed is:

1. A module for capturing at least one gas dissolved in a liquid arranged to be mounted on a body of a device for measuring the value of at least one parameter of said gas, said capturing module comprising:
   a gas circulation base arranged to be mounted on said body;
   the capturing module comprises a housing for receiving at least one membrane, said housing having an opening and said housing projecting from said base; and
   at least one membrane mounted in said housing so as to extend in said opening in order to capture the gas dissolved in the liquid.

2. The capturing module according to claim 1, wherein the housing extends perpendicular to the base.

3. The capturing module according to claim 1, comprising a porous membrane support element that is arranged in the opening of the housing and through which the gas can circulate.

4. The capturing module according to claim 3, comprising a gas injection conduit, connecting the support element of the membrane and the base, and which is configured to be in fluid communication with a gas inlet conduit of a body of a measuring device, and a gas discharge conduit, connecting the base to the support element of the membrane and which is configured to be in fluid communication with a gas outlet conduit of a body of a measuring device.

5. The capturing module according to claim 4, wherein the support element assumes the form of a planar plate extending in a parallel plane containing the longitudinal axis of the gas injection conduit and the longitudinal axis of the gas discharge conduit.

6. The capturing module according to claim 4, wherein the support element comprises, on its periphery, a machined gas outlet wall emerging on the gas injection conduit and a machined gas inlet wall emerging on the gas discharge conduit.

7. A module for capturing at least one gas dissolved in a liquid arranged to be mounted on a body of a device for measuring the value of at least one parameter of said gas, said capturing module comprising:
   a gas circulation base arranged to be mounted on said body;
   the capturing module comprises a housing for receiving at least one membrane, said housing having an opening and said housing projecting from said base;
   at least one membrane mounted in said housing so as to extend in said opening in order to capture the gas dissolved in the liquid;
   a porous membrane support element arranged in the opening of the housing and through which gas can circulate; and
   wherein the opening of the housing is a through opening and in that the capturing module comprises two membranes arranged on either side of the support element.

8. A device for measuring the value of at least one parameter of at least one gas dissolved in a liquid, said device comprising a hollow body, in which a measuring sensor is mounted, and a capturing module, according to claim 1, mounted on said body by its base, said device configured to be submerged in a liquid.

9. The device according to claim 8, wherein the body of the device being cylindrical, the membrane extends in a plane parallel to the longitudinal axis of said body.

10. The device according to claim 8, wherein the capturing module assumes the form of a stopper mounted on one end of the body of the measuring device.

11. The module of claim 7, where the gas circulating base comprises a planar wall surface with a perimeter.

12. The module of claim 7, wherein the housing comprises two channels formed in the body of the housing, the two channels being located along opposite edges of the opening of the housing.

13. A device for measuring a value of at least one parameter of at least one gas dissolved in a liquid, said device comprising:
   a body comprising a wall defining an interior and at least one open end;
   a module sized and shaped for coupling to the open end of the body, said module for capturing at least one gas and comprising:
      a base comprising a planar wall surface and a perimeter surrounding the planar wall surface;
      a housing extending radially of the planar wall surface of the base and away from the interior of the body; said housing having a structure with a perimeter and said structure comprising a perimeter defining a through opening; and
      at least one membrane mounted in said housing so as to extend in said through opening to capture said at least one gas when said device is submerged in a liquid.

14. The device of claim 13, further a support element located in said housing of said module and wherein the at least one membrane positioned against the support element.

15. The device of claim 14, wherein the at least one membrane is a first membrane and further comprising a second membrane positioned against the support element opposite the first membrane.

16. The device of claim 15, further comprising a conduit formed in the housing, said conduit in fluid communication with a gas inlet conduit or a gas outlet conduit, the gas inlet conduit or the gas outlet conduit extending into the interior of the body.

17. The device of claim 13, wherein the base comprises a plurality of bosses each having a screw located therein for connecting to the body.

18. The device of claim 15, further comprising a gasket located between the housing and the first membrane and a second gasket located between the housing and the second membrane.

19. The device of claim 14, wherein the support element is a porous disc.

20. The device of claim 19, wherein the support element is a metal porous disc formed by sintering.

* * * * *